US006683187B2

(12) United States Patent
De Boer et al.

(10) Patent No.: US 6,683,187 B2
(45) Date of Patent: Jan. 27, 2004

(54) LIGANDS AND CATALYST SYSTEMS THEREOF FOR ETHYLENE OLIGOMERIZATION TO LINEAR ALPHA OLEFINS (75) Inventors: Eric Johannes Maria De Boer, Amsterdam (NL); Harry Van Der Heijden, Amsterdam (NL); Nicolaas Meijboom, Amsterdam (NL); Arie van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 19 days.

(21) Appl. No.: 09/894,680

(22) Filed: Jun. 28, 2001

(65) Prior Publication Data

US 2002/0028941 A1 Mar. 7, 2002

(30) Foreign Application Priority Data

Jun. 30, 2000  (EP) .............................................. 00305543

(51) Int. Cl.[7] .......................................... C07D 213/61
(52) U.S. Cl. ..................................................... 546/345
(58) Field of Search ............................ 546/329, 9, 345

(56) References Cited

FOREIGN PATENT DOCUMENTS

| WO | WO 9827124 | * | 6/1988 | |
| WO | WO 98/27124 | | 6/1998 | ............ C08F/10/00 |
| WO | 9827124 | * | 6/1998 | |
| WO | WO 99/02472 | | 1/1999 | ............. C07C/2/32 |
| WO | WO 00/15646 | | 3/2000 | ............ C07F/13/00 |

OTHER PUBLICATIONS

"Oligomerization of Ethylene to Higher Linear α–Olefins," by Dieter Vogt, *Applied Homogeneous Catalysis With Organometallic Compounds*, Edited by Boy Cornils and Wolfgang A. Herrmann, vol. 1, Ch. 2.3.1.3, pp. 245–258, VCH 1996.

"Novel, Highly Active Iron and Cobalt Catalysts for Olefin Polymerization," by Alison M. A. Bennett, *Chemtech* Jul. 1999, pp. 24–28.

* cited by examiner

*Primary Examiner*—Alan L. Rotman
*Assistant Examiner*—Binta Robinson

(57) ABSTRACT

Ligands of formula (V);

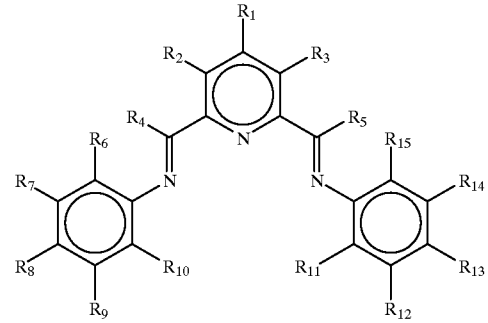

bis-aryliminepyridine $MX_n$ complexes comprising a ligand of formula (V), wherein M is a metal selected from Fe and Co, n is 2 or 3, and X is halide, optionally substituted hydrocarbyl, alkoxide, amide, or hydride; [bis-aryliminepyridine $MY_p.L_n^+$] $[NC^{31}]_q$ complexes, comprising a ligand of formula (V), wherein Y is a ligand which may insert an olefin, M is Fe or Co, $NC^-$ is a non-coordinating anion and p+q is 2 or 3, matching the formal oxidation of the metal atom M, L is a neutral Lewis donor molecule and n=0, 1, or 2; and processes for the production of alpha-olefins from ethylene, using said complexes.

48 Claims, 3 Drawing Sheets

US 6,683,187 B2

LIGANDS AND CATALYST SYSTEMS THEREOF FOR ETHYLENE OLIGOMERIZATION TO LINEAR ALPHA OLEFINS

FIELD OF THE INVENTION

The present invention relates to ligands, various catalyst precursors and catalyst systems derived from these ligands for ethylene oligomerisation to linear alpha olefins in high yield and very high selectivity, and a process for preparing said linear alpha olefins.

BACKGROUND OF THE INVENTION

Various processes are known for the production of higher linear alpha olefins (for example D. Vogt, *Oligomerisation of ethylene to higher α-olefins* in Applied Homogeneous Catalysis with Organometallic Compounds Ed. B. Cornils, W. A. Herrmann Vol. 1, Ch. 2.3.1.3, page 245, VCH 1996).

These commercial processes afford either a Poisson or Schulz-Flory oligomer product distribution. In order to obtain a Poisson distribution, no chain termination must take place during oligomerisation. However, in contrast, in a Schulz-Flory process, chain termination does occur and is independent of chain length. The Ni-catalysed ethylene oligomerisation step of the Shell Higher Olefins Process (SHOP) is a typical example of a Schulz-Flory process.

In a Schulz-Flory process, a wide range of oligomers are typically made in which the fraction of each olefin can be determined by calculation on the basis of the so-called K-factor. The K-factor, which is indicative of the relative proportions of the product olefins, is the molar ratio of $[C_{n+2}]/[C_n]$ calculated from the slope of the graph of log $[C_n$ mol %] versus n, where n is the number of carbon atoms in a particular product olefin. The K-factor is by definition the same for each n. By ligand variation and adjustment of reaction parameters, the K-factor can be adjusted to higher or lower values. In this way, the process can be operated to produce a product slate with an optimised economic benefit. Since demand for the $C_6$–$C_{18}$ fraction is much higher than for the $C_{>20}$ fraction, processes are geared to produce the lower carbon number olefins. However, the formation of the higher carbon number olefins is inevitable, and, without further processing, the formation of these products is detrimental to the profitability of the process.

To reduce the negative impact of the higher carbon number olefins and of the low value $C_4$ fraction, additional technology has been developed to reprocess these streams and convert them into more valuable chemicals such as internal $C_6$–$C_{18}$ olefins. However, this technology is expensive both from an investment and operational point of view and consequently adds additional cost. Therefore it is desirable to keep the production of the higher carbon number olefins to the absolute minimum, i.e. not more than inherently associated with the Schulz-Flory K-factor.

WO-A-98/27124 discloses iron- and cobalt-based ethylene polymerisation catalysts. Said catalysts comprise iron and cobalt complexes of 2,6-pyridinecarboxaldehydebis (imines) and 2,6-diacylpyridinebis(imines) of the formula (I):

wherein M is Co or Fe; each X is an anion; n is 1, 2, or 3, so that the total number of negative charges on said anion or anions is equal to the oxidation state of a Fe or Co atom present in (I); $R^1$, $R^2$ and $R^3$ are each independently hydrogen, hydrocarbyl, substituted hydrocarbyl, or an inert functional group; $R^4$ and $R^5$ are each independently hydrogen, hydrocarbyl, an inert functional group or substituted hydrocarbyl; $R^6$ is of formula (II);

$R^7$ is of formula (III);

$R^8$ and $R^{13}$ are each independently hydrocarbyl, substituted hydrocarbyl or an inert functional group; $R^9$, $R^{10}$, $R^{11}$, $R^{14}$, $R^{15}$ and $R^{16}$ are each independently hydrogen, hydrocarbyl, substituted hydrocarbyl or an inert functional group; $R^{12}$ and $R^{17}$ are each independently hydrogen, hydrocarbyl, substituted hydrocarbyl or an inert functional group; and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

$R^8$ and $R^{13}$ are each preferably alkyl groups containing from 1 to 6 carbon atoms, and more preferably iso-propyl or tert-butyl groups. $R^{12}$ and $R^{17}$ are each preferably alkyl groups containing from 1 to 6 carbon atoms, and more preferably iso-propyl groups.

The polymerisation process of WO-A-98/27124 produces both oligomers and polymers of ethylene. Said products may vary greatly in molecular weight. For example, whilst Example 32 in WO-A-98/27124 illustrates the production of oligomeric olefins, in particular decenes, the majority of the Examples therein produce lower molecular weight polyethylene oils and waxes and higher molecular weight polyethylenes.

Preferred products of WO-A-98/27124 are those with a degree of polymerisation (DP) of about 10 or more, preferably about 40 or more. By "DP" is meant the average number of repeat (monomer) units in a polymer molecule.

Thus, on the whole, the catalysts and process of WO-A-98/27124 are particularly directed towards the production of polymers of ethylene.

In WO-A-99/02472, there are disclosed novel iron-based ethylene oligomerisation catalysts that show high activity and high selectivity towards linear alpha olefins. The catalysts are based on iron complexes of a selected 2,6-pyridinedicarboxaldehyde bisimine or a selected 2,6-diacylpyridine bisimine.

In the present invention the term "bis-(aryliminoalkyl) pyridine", or in short, "bis-aryliminepyridine" is used to describe both classes of ligands.

In WO-A-99/02472, the oligomer product distribution made with these catalysts is not specified any further, but is implied to be Schulz-Flory in view of the definition, the use, and the determination of the Schulz-Flory K-factor.

In other publications, such as A. M. A. Bennett *Chemtech* 1999 July, page 24–28; and references mentioned therein, the product composition was stated to obey a Schulz-Flory distribution. The accompanying experimental data in WO-A-99/02472, however, shows that these catalysts afford a product slate with a surprisingly large amount of heavy products.

Further experimenting and analyses have confirmed that the disclosed oligomerisation catalysts afford a product composition which, in comparison with a Schulz-Flory distribution, indeed contains significantly more heavy products than expected.

Table 1 on page 30 of WO-A-99/02472 gives an overview of ethylene oligomerisation experiments catalysed by four different iron complexes (X–XIII). Experiment numbers 16 and 17 of this Table, in which iron complex XI is being used at ethylene pressure of 1.4 MPa (gauge) or 1.5 MPa (15 bar(a)) and 2.8 MPa (gauge) or 2.9 MPa (29 bar(a)) respectively, both give rise to a Schulz-Flory K-factor of 0.79, as derived from the $C_{16}/C_{14}$ ratio. If it is assumed that a perfect Schulz-Flory distribution is obtained in these experiments, that is to say $C_{n+2}/C_n$=K=0.79, it can be calculated that the $C_{30}$–$C_{100}$ fraction is 15% wt. and the $C_{20}$–$C_{28}$ fraction is 21% wt. on total product. If it is further assumed that the solids mentioned in Table 1 contain the $C_{20}$–$C_{100}$ fraction then this should amount to 36% wt. on total product. This should be considered as a maximum solids content since at least the major part of the lowest ethylene oligomers in this fraction remain dissolved in the toluene-solution of the $C_4$–$C_{18}$ fraction. In Experiment numbers 16 and 17 of Table 1, however, the amount of solids isolated are 14.1 g and 18.0 g, which may be calculated as a solids content of 45% wt. and 58% wt. on total product, respectively.

Similarly for a K-factor of 0.81 it can be calculated that the $C_{20}$–$C_{28}$ fraction and the $C_{30}$–$C_{100}$ fraction are 22% wt. and 20% wt. on total product, respectively, or maximally 42% wt. for the solids content. For Experiment number 18 in Table 1, also using iron complex XI, but now at pressure of 0 MPa (gauge), i.e. 0.1 MPa (1 bar(a)), the amounts of solids isolated are 2.7 g, which may be calculated as a solids content of 54% wt. on total product.

The distributions obtained in Experiment numbers 16–18 in Table 1 of WO-A-99/02472 clearly indicate that larger quantities of higher carbon number products, i.e. solids (>$C_{20}$), are produced than would be expected on the basis of the Schulz-Flory K-factor.

The excess of heavy ends has a detrimental effect on the economics of the technology.

In European Patent Application No. 00301036.0, provides a bis-aryliminepyridine $MX_n$ complex comprising a non-symmetrical ligand of formula (IV):

(IV)

wherein M is a metal atom selected from Fe or Co; n is 2 or 3; X is halide, optionally substituted hydrocarbyl, alkoxide, amide, or hydride; $R_1$–$R_5$, $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring; $R_6$ is hydrogen, optionally substituted hydrocarbyl, an inert functional group, or taken together with $R_7$ or $R_4$ to form a ring; $R_{10}$ is hydrogen, optionally substituted hydrocarbyl, an inert functional group, or taken together with $R_9$ or $R_4$ to form a ring; and $R_{11}$ and $R_{15}$ are, independently, hydrogen or an inert functional group.

The term "non-symmetrical" is used in relation to the four ortho-positions of the two aryl-imino groups and defines these as such that neither the substitution pattern nor the substituents themselves afford two equally ortho-substituted aryl-imino groups.

SUMMARY OF THE INVENTION

A bis-ariyliminepyridine ligand of formula (V) is provided, (V)

wherein $R_1$–$R_5$ and $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring, and $R_6$, $R_{10}$, $R_{11}$ and $R_{15}$ are identical and are selected from fluorine or chlorine. Futher, a bis-aryliminepyridine $MX_n$ complex comprising the ligand of formula (V) and a [bis-aryliminepyridine $MY_p \cdot L_n^+$] [$NC^-$]$_q$ complex comprising the ligand of formula (V), wherein M is a metal atom selected from Fe and Co, X is halide, optionally subsituted hydrocarbyl, alkoxide, amide, or hydride with n of 2 or 3, Y is a ligand which my insert an olefin, $NC^-$ is a non-coordinating anion, and L is a neutral Lewis donor with n of 0, 1, or 2, are provided. Further, a process for the production of alpha-olefins using one or more such complexes are provided.

DETAILED DESCRIPTION OF THE INVENTION

There has now been surprisingly found a further class of novel bis-aryliminepyridine catalysts which not only display a high activity with respect to ethylene oligomerisation, but which also produce ethylene oligomers according to a Schulz-Flory distribution.

The present invention provides a bis-aryliminepyridine ligand of formula (V), wherein $R_1$–$R_5$, $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring; and $R_6$, $R_{10}$, $R_{11}$ and $R_{15}$ are identical and are selected from fluorine or chlorine.

(V)

The present invention further provides a bis-aryliminepyridine $MX_n$ complex comprising a ligand of formula (V), wherein M is a metal atom selected from Fe and Co, n is 2 or 3, and X is halide, optionally substituted hydrocarbyl, alkoxide, amide, or hydride.

In a further aspect, the present invention provides a process for the production of alpha-olefins, which comprises contacting one or more bis-aryliminepyridine $MX_n$ complexes of the present invention with ethylene and a second compound which is capable of transferring an optionally substituted hydrocarbyl or hydride group to said metal atom M, and which is also capable of abstracting an $X^-$ group from said metal atom, at a temperature in the range of $-100°$ C. to $300°$ C.

In a still further aspect, the present invention provides a process for the production of alpha-olefins, which comprises contacting one or more bis-aryliminepyridine $MX_n$ complexes of the present invention with ethylene and a second compound which is capable of transferring an optionally substituted hydrocarbyl or hydride group to said metal atom M, and a third compound which is capable of abstracting an $X^-$ group from said metal atom, at a temperature in the range of $-100°$ C. to $+300°$ C.

The present invention further provides a [bis-aryliminepyridine $MY_p.L_n^+$] [$NC^-$]$_q$ complex comprising a ligand of formula (V), wherein Y is a ligand which may insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

The present invention further provides a process for the production of alpha-olefins, comprising contacting one or more [bis-aryliminepyridine $MY_p.L_n^+$] [$NC^-$]$_q$ complexes of the present invention with ethylene at a temperature in the range of $-100°$ C. to $+300°$ C.

In the present invention certain terms are used as follows:

Hydrocarbyl group: a group containing only carbon and hydrogen. Unless otherwise stated, the number of carbon atoms is preferably between 1 and 30.

In the present invention, the phrase "optionally substituted hydrocarbyl" is used to describe hydrocarbyl groups optionally containing one or more "inert" heteroatom-containing functional groups. By "inert" is meant that the functional groups do not interfere to any substantial degree with the oligomerisation process. Non-limiting examples of such inert groups are fluoride, chloride, silanes, stannanes, ethers and amines with adequate steric shielding, all well-known to those skilled in the art. Said optionally substituted hydrocarbyl may include primary, secondary and tertiary carbon atom groups of the nature described below.

Inert functional group: a group other than optionally substituted hydrocarbyl which is inert under the process conditions. By "inert" is meant that the functional group does not interfere to any substantial degree with the oligomerisation process. Examples of inert functional groups include halide, ethers, and amines, in particular tertiary amines.

Primary carbon atom group: a —$CH_2$—R group wherein R may be hydrogen, a optionally substituted hydrocarbyl, inert functional group. Examples of primary carbon atom groups include —$CH_3$, —$C_2H_5$, —$CH_2Cl$, —$CH_2OCH_3$, $CH_2N(C_2H_5)_2$, —$CH_2Ph$.

Secondary carbon atom group: a —CH—$R_2$ group wherein R may be optionally substituted hydrocarbyl, inert functional group. Examples of secondary carbon atom groups include —$CH(CH_3)_2$, —$CHCl_2$, —$CHPh_2$, —$CH=CH_2$, cyclohexyl.

Tertiary carbon atom group: a —C—$R_3$ group wherein R may be optionally substituted hydrocarbyl, inert functional group. Examples of tertiary carbon atom groups include —$C(CH_3)_3$, —$CCl_3$, —$C\equiv CPh$, 1-Adamantyl, —$C(CH_3)_2$ ($OCH_3$).

By a "ligand which may insert an olefin" is meant a ligand which is coordinated to a metal ion into which bond an ethylene molecule may be inserted to initiate or propagate an oligomerisation reaction. In [bis-aryliminepyridine $MY_p.L_n^+$] [$NC^-$]$_q$ complexes according to the present invention, Y may be hydride, alkyl or any other anionic ligand which may insert an olefin.

By "non-coordinating anion" is meant an anion which does not substantially coordinate to the metal atom M. Non-coordinating anions ($NC^-$) that may be suitably employed include bulky anions such as tetrakis [3,5 bis (trifluoromethyl)phenyl]borate ($BAF^-$), ($C_6F_5)_4B^-$, and anions of alkylaluminium compounds including $R_3AlX^-$, $R_2AlClX^-$, $RAlCl_2X^-$, and "$RAlOX^-$", wherein R is hydrogen, optionally substituted hydrocarbyl or an inert functional group, and X is halide, alkoxide or oxygen.

It will be appreciated by those skilled in the art that within the boundary conditions herein before described, substituents $R_1$–$R_{15}$ may be readily selected to optimize the performance of the catalyst system and its economical application.

Substituents $R_1$–$R_5$, $R_7$–$R_9$, $R_{12}$–$R_{14}$ may independently be linked together and form cyclic structures.

Furthermore it will be readily appreciated by any person who has mastered the basic principles of homogeneous catalysis that substituent variations of $R_1$–$R_5$, $R_7$–$R_9$, and $R_{12}$–$R_{14}$ may be selected so as to enhance other desirable properties of catalyst precursors and catalyst systems such as solubility in non-polar solvents or extending the range of suitable starting materials in their syntheses.

Preferred embodiments of this invention are ligands according to (V) and derivatives thereof, in which the following R groups appear: $R_1$–$R_3$ are hydrogen; and/or $R_4$ and $R_5$ are methyl, hydrogen, benzyl or phenyl, preferably methyl, phenyl or hydrogen.

In a preferred embodiment, a ligand of formula (V) is provided, wherein $R_1$–$R_3$ are hydrogen; $R_4$ and $R_5$ are methyl; $R_7$–$R_9$ and $R_{12}$–$R_{14}$ are hydrogen; and $R_6$, $R_{10}$, $R_{11}$ and $R_{15}$ are fluorine.

In another preferred embodiment, a ligand of formula (V) is provided, wherein $R_1$–$R_3$ are hydrogen; $R_4$ and $R_5$ are hydrogen; $R_7$–$R_9$ and $R_{12}$–$R_{14}$ are hydrogen; and $R_6$, $R_{10}$, $R_{11}$ and $R_{15}$ are fluorine.

In another preferred embodiment, a ligand of formula (V) is provided, wherein $R_1$–$R_3$ are hydrogen; $R_4$ and $R_5$ are methyl; $R_7$–$R_9$ and $R_{12}$–$R_{14}$ are hydrogen; and $R_6$, $R_{10}$, $R_{11}$ and $R_{15}$ are chlorine.

In another preferred embodiment, a ligand of formula (V) is provided, wherein $R_1$–$R_3$ are hydrogen; $R_4$ and $R_5$ are hydrogen; $R_7$–$R_9$ and $R_{12}$–$R_{14}$ are hydrogen; and $R_6$, $R_{10}$, $R_{11}$ and $R_{15}$ are chlorine.

In another preferred embodiment, a ligand of formula (V) is provided, wherein $R_1$–$R_3$ are hydrogen; $R_4$ and $R_5$ are phenyl; $R_7$–$R_9$ and $R_{12}$–$R_{14}$ are hydrogen; and $R_6$, $R_{10}$, $R_{11}$ and $R_{15}$ are chlorine.

In yet another preferred embodiment, a ligand of formula (V) is provided, wherein $R_1$–$R_3$ are hydrogen; $R_4$ and $R_5$ are phenyl; $R_7$–$R_9$ and $R_{12}$–$R_{14}$ are hydrogen; and $R_6$, $R_{10}$, $R_{11}$ and $R_{15}$ are fluorine.

In the derived bis-aryliminepyridine $MX_n$ complex, X may conveniently be halide, preferably, chlorine.

In a preferred embodiment of the bis-aryliminepyridine $MX_n$ complex, metal atom M is Fe and n is 2. In another preferred embodiment, metal atom M is Fe and n is 3.

Compounds which are capable of transferring an optionally substituted hydrocarbyl or hydride group to metal atom M, and which are also capable of abstracting an $X^-$ group from metal atom M include alkylaluminium compounds such as alkylaluminoxane and alkylaluminium halides. A preferred compound is methylaluminoxane.

Compounds which are capable of transferring an optionally substituted hydrocarbyl or hydride group to metal atom M include alkylaluminium compounds including alkyl aluminoxanes, alkyl lithium compounds, Grignards, alkyl tin and alkyl zinc compounds.

Compounds which are capable of abstracting an $X^-$ group from metal atom M include strong neutral Lewis acids such as $SbF_5$, $BF_3$ and $Ar_3B$, wherein Ar is a strong electron-withdrawing aryl group such as $C_6F_5$ or $3,5\text{-}(CF_3)_2C_6H_3$.

A neutral Lewis donor molecule is a compound which may suitably act as a Lewis base, such as ethers, amines, sulphides and organic nitrites.

In the [bis-aryliminepyridine $MY_p.L_n^+$] [$NC^-$]$_q$ complex according to the present invention, L may be a neutral Lewis donor molecule capable of being displaced by ethylene, or a vacant coordination site.

In the [bis-aryliminepyridine $MY_p.L_n^+$] [$NC^-$]$_q$ complex according to the present invention, metal atom M is preferably Fe and the formal oxidation state of said metal atom may be 2 or 3.

It will be appreciated that a further advantage of catalysts and ligands according to the present invention is that they may be more readily synthesised than the previously described non-symmetrical catalysts and ligands developed for the production of ethylene oligomers according to a Schulz-Flory distribution.

The catalyst system may be formed by mixing together the complex and optional additional compounds, preferably in a solvent such as toluene or isooctane.

The mole ratio of complex, second compound, and optionally third compound is not limited in the present invention.

As illustrated herein, it is possible to enhance the flexibility of an ethylene oligomerisation reaction by employing a catalyst mixture comprising a catalyst according to the present invention and one or more catalysts previously known in the art, and in particular one or more previously described catalysts as cited herein. Such a method may be used, for example, to increase the $C_4$–$C_{10}$ content of an alpha olefin mixture normally produced using the prior art catalysts and/or previously described catalysts, whilst maintaining alpha olefin purity.

Thus, in a preferred embodiment of the present invention there is provided a process for the production of alpha olefins, wherein one or more complexes of the present invention are contacted with one or more additional complexes that may be suitably employed in the production of alpha olefins.

Such a quantity of the catalyst system is usually employed in the oligomerisation reaction mixture so as to contain from $10^{-4}$ to $10^{-9}$ gram atom, of metal atom M, in particular of Fe [II] or [III] metal per mole of ethylene to be reacted.

The oligomerisation reaction may be most conveniently conducted over a range of temperatures from −100° C. to 300° C., preferably in the range of from 0° C. to 200° C., and more preferably in the range of from 50° C. to 150° C.

The oligomerisation reaction may be conveniently carried out at a pressure of 0.01 to 15 MPa (0.1 to 150 bar(a)), more preferably 1 to 10 MPa (10 to 100 bar(a)), and most preferably 1 to 5 MPa (10 to 50 bar(a)).

The optimum conditions of temperature and pressure used for a particular catalyst system to maximise the yield of oligomer, and to minimise the competing reactions such as dimerisation and polymerisation can be readily established by one skilled in the art.

The conditions of temperature and pressure are preferably selected to yield a product slate with a K-factor within the range of from 0.40 to 0.90, preferably in the range of from 0.45 to 0.90. In the present invention, polymerisation is deemed to have occurred when a product slate has a K-factor greater than 0.9.

The oligomerisation reaction can be carried out in the gas phase or liquid phase, or mixed gas-liquid phase, depending upon the volatility of the feed and product olefins.

The oligomerisation reaction is carried out in the presence of an inert solvent which may also be the carrier for the catalyst and/or feed olefin. Suitable solvents include alkanes, alkenes, cycloalkanes, and aromatic hydrocarbons. For example, solvents that may be suitably used according to the present invention include hexane, isooctane, benzene, toluene, and xylene.

Reaction times of from 0.1 to 10 hours have been found to be suitable, dependent on the activity of the catalyst. The reaction is preferably carried out in the absence of air or moisture.

The oligomerisation reaction may be carried out in a conventional fashion. It may be carried out in a stirred tank reactor, wherein olefin and catalyst or catalyst precursors are added continuously to a stirred tank and reactant, product, catalyst, and unused reactant are removed from the stirred tank with the product separated and the catalyst and unused reactant recycled back to the stirred tank.

Alternatively, the reaction may be carried out in a batch reactor, wherein the catalyst precursors, and reactant olefin are charged to an autoclave, and after being reacted for an appropriate time, product is separated from the reaction mixture by conventional means, such as distillation.

After a suitable reaction time, the oligomerisation reaction can be terminated by rapid venting of the ethylene in order to deactivate the catalyst system.

The resulting alpha olefins may have a chain length of from 4 to 100 carbon atoms, preferably 4 to 30 carbon atoms, and most preferably from 4 to 20 carbon atoms.

Product olefins can be recovered suitably by distillation and further separated as desired by distillation techniques dependent on the intended end use of the olefins.

It may be stated that in the case of using a 2,6-bis[1-(2,6-dihaloarylimine)alkyl]pyridine catalyst according to the present invention, no deviation from Schulz-Flory distribution occurs. This is beneficial to the economics of the overall process, as in this case no additional amounts of solids, that is to say, heavy wax, are being formed which may be cumbersome due to clogging, etc. of the plant and/or its work-up train. Such solids normally require processing by isomerisation and disproportionation with, for example, 2-butene to arrive at internal olefins in the economically attractive range ($C_8$–$C_{20}$).

Moreover, the ease of preparation and the catalyst activity of these new catalysts is at least on a par with the cited catalysts, published previously.

Figure 1:
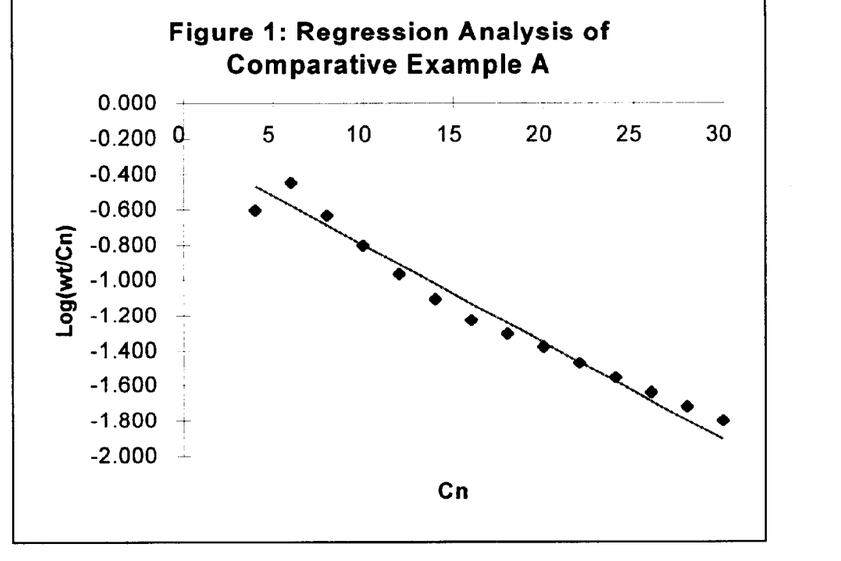
FIG. 1 is a regression analysis of Example A (comparative).
Figure 2:
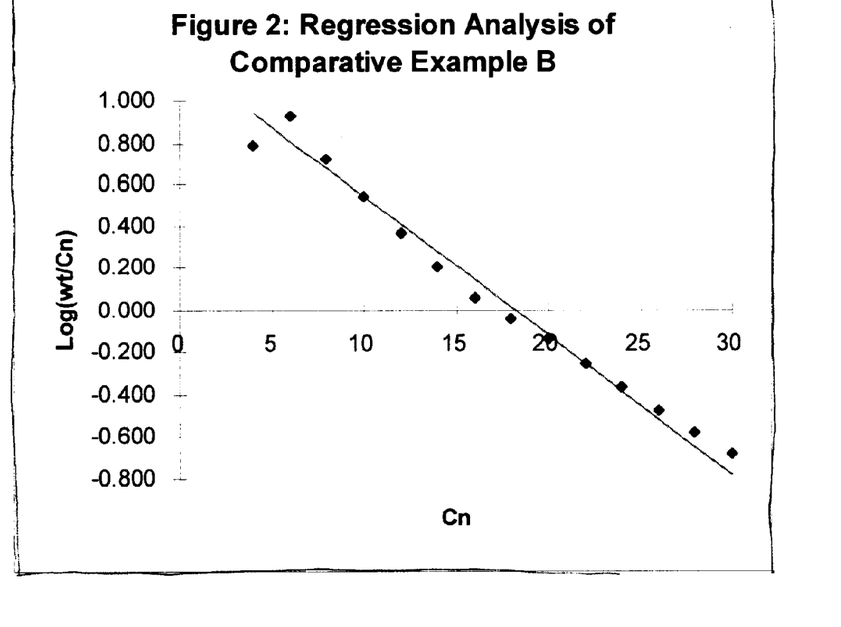
FIG. 2 is a regression analysis of Example B (comparative).
Figure 3:
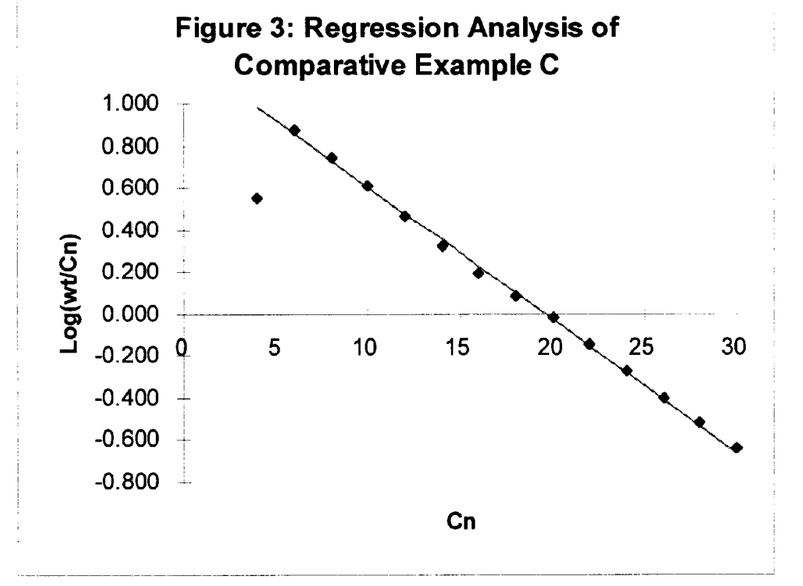
FIG. 3 is a regression analysis of Example C (comparative).
Figure 4:
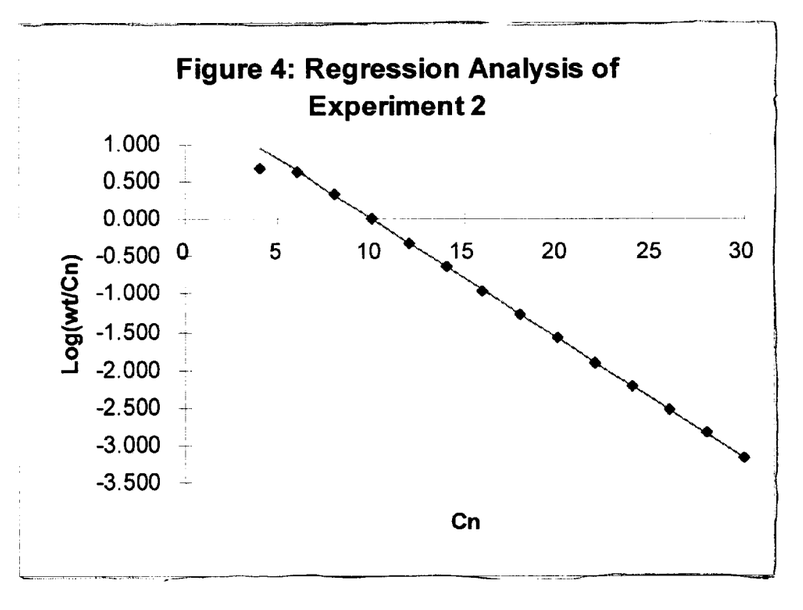
FIG. 4 is a regression analysis of Experiment 2.

The present invention will now be illustrated by the following Examples, which should not be regarded as limiting the scope of the invention in any way, by reference to the accompanying drawings, in which:

FIG. 1 is a regression analysis of Example A (comparative);

FIG. 2 is a regression analysis of Example B (comparative);

FIG. 3 is a regression analysis of Example C (comparative);

FIG. 4 is a regression analysis of Experiment 2; and

Figure 5:
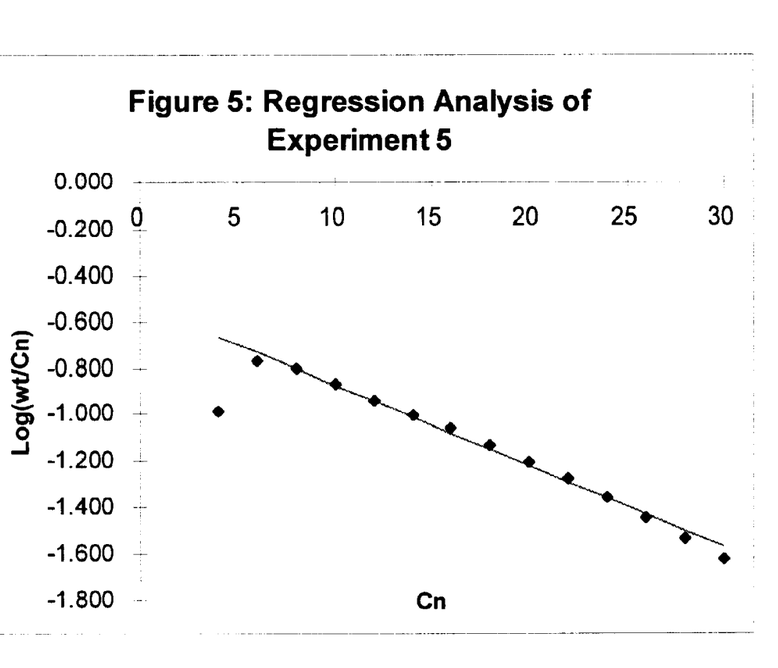
FIG. 5 is a regression analysis of Experiment 5.

FIG. 5 is a regression analysis of Experiment 5.

General Procedures and Characterisation

All the operations with the catalyst systems were carried out under nitrogen atmosphere. All solvents used were dried using standard procedures.

In particular, anhydrous toluene (99.8% purity) (ex. Aldrich) was dried over 4 Å molecular sieves (final water content of about 3 ppm).

Ethylene (99.5% purity) was purified over a column containing 4 Å molecular sieves and BTS catalyst (ex. BASF) in order to reduce water and oxygen content to <1 ppm.

2,6-Diacetylpyridine, 2,6-diformylpyridine, 2,4,6-trimethylaniline, 4-tert-butylaniline, 2,6-difluoroaniline, 2,6-dichloroaniline and anhydrous iron (II) chloride are available ex. Aldrich.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. Response factors for the even linear alpha-olefins relative to n-hexylbenzene (internal standard) were determined using a standard calibration mixture. The yields of the $C_4$–$C_{30}$ olefins were obtained from the GC analysis, from which the K-factor and the theoretical yield of $C_4$–$C_{100}$ olefins, i.e. total oligomerisation product (Total Product), were determined by regression analysis, using the $C_6$–$C_{28}$ data.

The relative amounts of the linear 1-hexene amongst all hexene isomers and the relative amount of 1-dodecene amongst all dodecene isomers found from the GC analysis is used as a measure of the selectivity of the catalyst towards linear alpha-olefin formation.

The NMR data were obtained at room temperature with a Varian 300 or 400 MHz apparatus.

Catalyst Components

1. Preparation of 2,6-bis-[1-(2-methylphenylimino) ethyl] pyridine iron[II] chloride complex (X) X was prepared according to the method disclosed in WO-A-99/02472.

2. Preparation of 2,6-bis-[1-(2-ethylphenylimino) ethyl] pyridine iron[II] chloride complex (XI) XI was prepared according to the method disclosed in WO-A-99/02472.

3. Preparation of 2-[1-(2,4,6-trimethylphenylimino) ethyl]-6-acetylpyridine (1)

(1)

2,6-Diacetylpyridine (7.3 g, 44.8 mmol) and 2,4,6-trimethylaniline (5.74 g, 42.55 mmol) were dissolved in 450 ml of toluene. To this solution, 4 Å molecular sieves and a small amount of p-toluenesulphonic acid (0.22 mmol) were added. The mixture was refluxed for 16 h. After filtration the solvent was removed in vacuo. Several crystallisations from ethanol yielded 3.42 g (28.7%) of monoimine (1). $^1$H-NMR (CDCl$_3$) δ 8.55 (d, 1H, Py-H$_m$), 8.11 (d, 1H, Py-H$_m$), 7.92 (t, 1H, Py-H$_p$), 6.89 (s, 2H, ArH), 2.77 (s, 3H, Me), 2.27 (s, 3H, Me), 2.22 (s, 3H, Me), 1.99 (s, 6H, Me).

4. Preparation of 2-[1-(2,4,6-trimethylphenylimino) ethyl]-6-[1-(4-tert-butylphenylimino)ethyl]pyridine (2)

(2)

Monoimine (1, 2.8 g, 10 mmol) and 4-tert-butylaniline (1.49 g, 10 mmol) were dissolved in 100 ml of toluene. To this solution, 4 Å molecular sieves and a small amount of p-toluenesulphonic acid (0.1 mmol) were added. After standing for 5 days with addition of more 4 Å molecular sieves, the mixture was refluxed for 2 h. After filtration the solvent was removed in vacuo. The residue was washed with methanol and recrystallised from ethanol. Yield 2.4 g (58%) of mixed diimine (2). $^1$H-NMR (CDCl$_3$) δ 8.42 (d, 1H, Py-H$_m$), 8.34 (d, 1H, Py-H$_m$), 7.86 (t, 1H, Py-H$_p$), 7.38 (d, 2H, ArH), 6.89 (s, 2H, ArH), 6.78 (d, 2H, ArH), 2.42 (s, 3H, Me), 2.29 (s, 3H, Me), 2.22 (s, 3H, Me), 2.00 (s, 6H, Me), 1.34 (s, 9H, Bu$^t$).

5. Preparation of 2-[1-(2,4,6-trimethylphenylimino) ethyl]-6-[1-(4-tert-butylphenylimino) ethyl] pyridine iron [II] chloride complex (3)

(3)

In an inert atmosphere a solution of 1.5 g diimine (2, 3.6 mmol) in 100 ml dichloromethane was added to 420 mg FeCl$_2$ (3.3 mmol) in 150 ml dichloromethane. The mixture was stirred for one week. The developed blue precipitate was isolated by filtration and dried in vacuo. Yield 1.5 g (84%) of iron complex (3). $^1$H-NMR (Cl$_2$CDCDCl$_2$, broad signals) δ 79.3 (1H, Py-H$_m$), 77.7 (1H, Py-H$_m$), 27.0 (1H, Py-H$_p$), 20.7 (3H, Me), 17.3 (6H, Me), 15.0 (2H, ArH), 14.3 (2H, ArH), 1.2 (9H, Bu$^t$), −2.6 (3H, MeC═N), −17.9 (2H, o-ArH), −32.1 (3H, MeC═N).

6. Preparation of 2,6-bis-[1-(2,6-difluorophenylimino) ethyl]pyridine (4)

(4)

2,6-Diacetylpyridine (1.76 g, 10.8 mmol) and 2,6-difluoroaniline (2.94 g, 22.8 mmol) were dissolved in 50 ml of toluene. To this solution 4 Å molecular sieves were added. After standing for 3 days, with addition of more 4 Å molecular sieves the mixture was filtered. The solvent was removed in vacuo. The residue was crystallised from ethanol. Yield of 4:1 g (24%). $^1$H-NMR (CDCl$_3$) δ 8.44 (d, 2H, Py-H$_m$), 7.90 (t, 1H, Py-H$_p$), 7.05 (m, 2H, ArH) 6.96 (m, 4H, ArH), 2.44 (s, 6H, Me). $^{19}$F-NMR (CDCl$_3$) δ −123.6

7. 2,6-bis-[1-(2,6-difluorophenylimino)ethyl] pyridine iron[II] chloride complex (5)

(5)

In an inert atmosphere 493 mg diimine (4, 1.27 mmol) was dissolved in 50 ml THF. FeCl$_2$ (162 mg, 1.28 mmol) in 10 ml THF was added. After stirring for 16 h at room temperature, the solvent was removed in vacuo. Toluene (100 ml) was added. The blue precipitate was isolated by filtration, washed with pentane and dried in vacuo. Isolated 0.5 g (76%) of iron complex 5. $^1$H-NMR (Cl$_2$CDCDCl$_2$, broad signals) δ 75.5 (2H, Py-H$_m$), 39.6 (1H, Py-H$_p$), 15.7 (4H, ArH), −11.6 (2H, ArH), −22.4 (6H, MeC═N). $^{19}$F-NMR (Cl$_2$CDCDCl$_2$) δ −70.3

7'. Alternate preparation of 2,6-bis-[1-(2,6-difluorophenylimino)ethyl] pyridine iron[II] chloride complex (5')

(5')

In an inert atmosphere a solution of 60 mg FeCl$_2$ (0.47 mmol) in 0.5 ml ethanol was slowly added to a solution of 260 mg diimine (4, 0.67 mmol) in a solvent mixture of 10 ml toluene and 6 ml pentane. The resulting blue precipitate was isolated by centrifugation, washed three times with toluene and dried in vacuo. Yield 210 mg (87%) of iron complex 5'. $^1$H-NMR (CD$_2$Cl$_2$, broad signals) δ 76.7 (2H, Py-H$_m$), 37.6 (1H, Py-H$_p$), 16.8 (4H, ArH), −10.2 (2H, ArH), −20.3 (6H, MeC═N). $^{19}$F-NMR (CD$_2$Cl$_2$) δ −75.

8. Preparation of 2,6-bis-[(2,6-dichlorophenylimino) methyl]pyridine (6)

(6)

2,6-Pyridinedicarboxaldehyde (1 g, 7.4 mmol) and 2,6-dichloroaniline (2.6 g, 16.0 mmol) were dissolved in 100 ml of toluene. To this solution 4 Å molecular sieves were added. After standing for 2 days, with addition of more 4 Å molecular sieves the mixture was filtered. The solvent was removed in vacuo. The residue was crystallised from ethanol. Yield 1.4 g (45%) of 6. $^1$H-NMR (CDCl$_3$) δ 8.53 (s, 2H, HC=N), 8.45 (d, 2H, Py-H$_m$), 8.02 (t, 1H, Py-H$_p$), 7.36 (d, 4H, ArH), 7.03 (t, 2H, ArH).

9. Preparation of 2,6-bis-[(2,6-dichlorophenylimino) methyl]pyridine iron[II] chloride complex (7)

(7)

In an inert atmosphere a solution of 6 (0.7 g, 1.65 mmol) in 10 ml dichloromethane was added to 0.2 g FeCl$_2$ (1.57 mmol) in 10 ml dichloromethane. The mixture was stirred for 16 h. The resulting grey-green precipitate was isolated by centrifugation, washed with pentane and dried in vacuo. Yield 0.7 g (80%) of iron complex 7. $^1$H-NMR (Cl$_2$CDCDCl$_2$, broad signals, selective data) δ 54.6 (2H, Py-H$_m$), 10.3 (4H, ArH), −4.6 (2H, ArH).

10. Preparation of 2,6-dibenzoylpyridine

Aluminium trichloride (5.1 g, 3.18 mmol) was added to a suspension of 2,6-bis(chlorocarbonyl)pyridine (3.7 g, 18 mmol) in 200 ml of benzene. The reaction mixture was heated to 60° C. and kept at that temperature for 4 h and subsequently for 16 h at room temperature. The mixture was poured into water, the organic layer was separated and evaporated to dryness. The residue was dissolved in CH$_2$Cl$_2$ and filtered. Removal of CH$_2$Cl$_2$ in vacuum yielded 3.0 g (58%) of product.

11. Preparation of 2,6-bis[(2,6-difluorophenylimino)- (phenyl) methyl]pyridine (8)

(8)

2,6-Dibenzoylpyridine (464 mg, 1.61 mmol) and 2,6-difluoroaniline (7.33 mg, 5.67 mmol) were dissolved in 30 ml of toluene. To this solution molecular sieves (4 Å) were added. After standing for 3 days at room temperature (with addition of more molecular sieves after 2 days) the mixture was filtered. The solvent was removed in vacuo. The residue was crystallised from ethanol. Yield 250 mg (30%) of 2,6-bis[(2,6-difluorophenylimino) (phenyl) methyl]pyridine 8 as a mixture of 3 isomers.

$^{19}$F-NMR (CDCl$_3$):

δ −122.4

δ −122.8 and 123.3

δ −123.2

12. Preparation of 2,6-bis(2,6-difluorophenylimino)- (phenyl) methyl]pyridine iron[II] chloride complex (9)

(9)

In an inert atmosphere a solution of 32 mg FeCl$_2$ (0.25 mmol) in 0.5 ml ethanol was slowly added to a solution of 166 mg diimine (isomeric mixture of 8, 0.32 mmol) in 4 ml toluene. The blue precipitate was isolated by centrifugation, washed three times with toluene and dried in vacuo. Yield 160 mg (~100%) of iron complex 9.

$^1$H-NMR (CD$_2$Cl$_2$, broad signals, selected data) δ 70.4 (2H, Py-H$_m$), 60.7 (1H, Py-H$_p$), 16.8 (4H, ArH), 8.6 (4H, ArH), −12.9 (2H, ArH). $^{19}$F-NMR (CD$_2$Cl$_2$) δ −67.5

13. Methylaluminoxane (MAO)

The MAO-solution (10.1% wt. in toluene, [Al] 4.97% wt.) used was ex. Witco GmbH, Bergkamen, Germany.

Catalyst System Preparation

Catalyst preparation was carried out under nitrogen in a Braun MB 200-G dry box.

The iron complex (typically about 10 mg) was placed in a reaction vessel; the MAO-solution (4.0 g), of the above mentioned grade, was added and stirred for 2 minutes. This yielded generally a dark-coloured solution, which sometimes contained some precipitate. Thereafter toluene (9.0 g) was added and the solution was stirred for another 15 min. Immediately hereafter, part of this solution was used in the oligomerisation reaction (see Table 1 for the amounts used).

Oligomerisation Experiments

Oligomerisation experiments were carried out in a 1-liter steel autoclave equipped with jacket cooling with a heating/cooling bath (ex. Julabo, model no. ATS-2) and a turbine/gas stirrer and baffles, or in a similarly equipped 0.5-liter steel autoclave (as indicated in Table 1 and the description of the experiment). In order to remove traces of water from the reactor, it was evacuated overnight at <10 Pa, at 70° C. The reactor was scavenged by introducing 250 ml toluene and MAO (0.3–1.2 g solution) and subsequent stirring at 50° C. under nitrogen pressure of 0.4–0.5 MPa for 30 min. The reactor contents were discharged via a tap in the base of the autoclave. The reactor was evacuated to 0.4 kPa and loaded with 250 ml toluene, in the case of a 1-liter reactor, and heated to 40° C. and pressurised with ethylene to the pressure indicated in Table 1 or in the description of the experiment. The MAO-solution (typically 0.5 g for the 1-liter reactor) was then added to the reactor and the stirring was continued for 30 minutes (for the 0.5-liter reactor the amounts of solvent and MAO were halved). The catalyst system prepared as described above and in an amount as described in Table 1, was introduced into the stirred reactor using an injection system, which was rinsed twice with 10 ml toluene. Addition of the catalyst solution resulted in an exotherm (generally 5–20° C.), which reached a maximum within 1 minute and was followed by rapid establishment of the temperature indicated in Table 1. Temperature and pressure were monitored throughout the reaction, as well as ethylene consumption, whilst maintaining a constant ethylene pressure. After consuming a certain volume ethylene, the oligomerisation was stopped by rapid venting of the ethylene, decanting the product mixture into a collection bottle using a tap in the base of the autoclave. Exposure of the mixture to air resulted in rapid deactivation of the catalyst.

After addition of n-hexylbenzene (0.5–3.5 g) as internal standard to the crude product the amount of $C_4$–$C_{30}$ olefins was determined by gas chromatography, from which the K-factor was determined by regression analysis, using the $C_6$–$C_{28}$ data. From this regression analysis, the theoretical contents of $C_{30}$–$C_{100}$ components, i.e. waxy solids, was calculated. These data are reported in Table 1.

The amount of solids in the product was determined as follows. The crude reaction product was centrifuged at 4000 rpm for 30 min after which the clear upper layer was decanted. The lower layer consisting of solid olefins, toluene and a minor amount of liquid olefins was mixed with 500 ml acetone and filtered off over a glass filter (porosity P3). The solid product was dried for 24 hours at 70° C. at <1 kPa, weighed and its <$C_{30}$ contents determined by gas chromatography of a 1,2-dichlorobenzene or a 1,2,4-trichlorobenzene solution of the solids. The amounts of solids reported in Table 1 are the isolated solids having a carbon number >$C_{28}$.

The relative amounts of the linear 1-hexene amongst all hexene isomers and the relative amount of 1-dodecene amongst all dodecene isomers were evaluated by GC analysis and are reported in Table 1.

EXAMPLE A (COMPARATIVE)

Iron complex XI (prepared according to WO-A-99/02472) was employed in toluene in an experiment similar to Experiment Number 16 of WO-A-99/02472. The catalyst gave an oligomerisation mixture having a K-factor of 0.774, as derived from regression analysis using the $C_6$–$C_{28}$ contents, determined by GC. $C_4$ is left out of the regression analysis, since its volatility hinders reliable GC-measurements. The details of Example A are given in Table 1. From this K-factor a $C_{20}$–$C_{28}$ fraction of 19.7% wt. and a $C_{30}$–$C_{100}$ fraction of 12.2% wt. on total product can be calculated. The amount of solids >$C_{28}$ on total ethylene intake was 53.8% wt. (the ethylene intake is assumed to be equal to the total oligomerisation product, i.e. $C_4$–$C_{100}$ olefins). This corroborates that the distribution deviates greatly from Schulz-Flory, giving rise to larger than expected amounts of higher molecular weight compounds, i.e. solid waxes. This deviation is also clear from FIG. 1 in which the regression analysis is represented graphically (for 12 observations $R^2$=0.97 and standard error=0.07).

EXAMPLE B (COMPARATIVE)

Using the iron complex X in an experiment similar to Experiment number 13 of Table 1 of WO-A-99/02472, similar phenomena were observed (see comparative Example B in Table 1 for details). The amount of solids (having a carbon number>$C_{28}$) isolated was 11.1% wt. on total product, whilst on the basis of the K-factor of 0.737 (as derived from the $C_6$–$C_{28}$ contents by regression analysis) a $C_{30}$–$C_{100}$ fraction of 7.0% wt. on total product has to be expected. Hence, a clear deviation from Schulz-Flory distribution, giving rise to a larger amount of high molecular weight compounds than calculated. The regression analysis using the $C_6$–$C_{28}$ contents, as given in FIG. 2 also shows a clear deviation from Schulz-Flory distribution at higher carbon numbers (for 12 observations $R^2$=0.98 and standard error=0.06).

EXAMPLE C (COMPARATIVE)

Example C was carried using the non-symmetrical iron complex 3 which is in accordance with our co-pending European Patent Application No. 00301036.0, under conditions similar to the above-mentioned Example B. Experimental details are given in Table 1. The regression analysis for Example C, using the $C_6$–$C_{28}$ contents, as shown in FIG. 3, gives a nearly perfect Schulz-Flory distribution over the whole range of oligomers. The K-factor is 0.747 (for 12 observations $R^2$=1.00 and standard error=0.02). This is confirmed by the amount of waxy solids >$C_{28}$ isolated on total product of 6.6% wt., whereas the K-factor gives rise to a $C_{30}$–$C_{100}$ fraction on total oligomerisation product of 8.2% wt. (the fact that less solids >$C_{28}$ are isolated than theoretically expected is due to their solubility in the toluene-solution of the <$C_{28}$ oligomers).

Experiment 1

Experiment 1 was carried out in a 1-liter steel autoclave at an ethylene pressure of 1.6 MPa and a temperature of 50° C., using the symmetrical 2,6-bis-[1-(2,6-difluorophenylimino)ethyl] pyridine iron[II] chloride complex (5), which is in accordance with the present invention, under conditions similar to the above-mentioned (comparative) Example A. Experimental details are given in Table 1. The regression analysis for Experiment 1, using the $C_6$–$C_{28}$ contents, gives a nearly perfect Schulz-Flory distribution over the whole range of oligomers. The K-factor is 0.497 (for 12 observations $R^2$=1.00 and standard error= 0.02). This is confirmed by the amount of waxy solids >$C_{28}$ isolated on total product of <0.1% wt., whereas the K-factor gives rise to a $C_{30}$–$C_{100}$ fraction on total oligomerisation product of 0.1% wt.

In conclusion it may be stated that no deviation from Schulz-Flory distribution is observed, which translates to the formation of less high molecular weight products in comparison with (comparative) Examples A–B. This has the advantage of more straightforward processing (less clogging by solids in the plants and its work-up train) and of less need for reprocessing of high molecular weight olefins (to render the technology economically feasible). Besides these advantages over (comparative) Examples A–B, the 2,6-bis-[1-(2,6-difluoroarylimine)alkyl]pyridine symmetrical iron derived catalysts according to the present invention are more efficiently prepared than that of (comparative) Example C, while at the same time catalyst activity and selectivity remain high.

Experiment 2

Experiment 2 is a repeat of Experiment 1, but now using a differently prepared iron complex 5'. Experimental details are mentioned in Table 1. Once again, regression analysis using the $C_6$–$C_{28}$ contents gives a nearly perfect Schulz-Flory distribution, as shown in FIG. 4, having K-factor of 0.482 and the following regression statistics for 12 observations: $R^2$=1.00 and standard error=0.01. The Schulz-Flory distribution is again confirmed by the isolated amount of waxy solids >$C_{28}$, which is lower than the amounts calculated from the K-factor. It is clear that the catalyst derived from complex 5' shows an even higher activity than that derived from complex 5.

Experiment 3

Experiment 3 is a repeat of Experiment 2, but at an average ethylene pressure of 1.1 MPa. Experimental details are mentioned in Table 1. Once again, regression analysis using the $C_6$–$C_{28}$ contents gives a nearly perfect Schulz-Flory distribution, having K-factor of 0.503 and the following regression statistics for 12 observations: $R^2$=1.00 and standard error=0.01. The Schulz-Flory distribution is yet again confirmed by the isolated amount of waxy solids >$C_{28}$, which is lower than the amounts calculated from the K-factor.

Experiment 4

In this Experiment, 132 nmol of complex 3 and 155 nmol of complex 5 were mixed and activated and the mixed catalyst was employed at an ethylene pressure of 1.6 MPa at 70° C., using a 0.5-liter steel autoclave. The experimental details are given in Table 1. From the Turn Over Frequency (T.O.F.) it is concluded that both types of catalysts are compatible with each other and that complex 5 can be employed to increase the $C_4$–$C_{10}$ content of the alpha olefin mixture normally produced with catalysts based on Complex 3. Application of a catalyst mixture largely increases the flexibility of an alpha olefin manufacturing process, whilst maintaining the alpha olefin purity (see Table 1).

Experiment 5

Experiment 5 with iron complex 7 was carried out in a 1-liter steel autoclave, using a mode of iron complex addition/activation similar to that described in Experiment number 20 of WO-A-99/02472. To that end 5.0 g of a toluene solution of iron complex 7 (10.7 mg of iron complex 7 in 9.0 g dry toluene) was added to the 1-liter autoclave, loaded with 250 ml of toluene and 4.5 g of MAO (see Table 1 for experimental details). The regression analysis for Experiment 5, using the $C_6$–$C_{28}$ contents, gives a nearly perfect Schulz-Flory distribution over the whole range of oligomers, as shown in FIG. 5. The K-factor is 0.851 (for 12 observations $R^2$=0.99 and standard error=0.02). The Schulz-Flory distribution is yet again confirmed by the isolated amount of waxy solids >$C_{28}$, which is lower than the amounts calculated from the K-factor.

Experiment 6

Experiment 6 was carried out in a 1-liter steel autoclave at an ethylene pressure of 1.6 MPa and a temperature of 50° C., using the symmetrical 2,6-bis-[(2,6-difluorophenylimino) (phenyl)methyl] pyridine iron[II] chloride complex (9), which is in accordance with the present invention, under conditions similar to the above-mentioned Comparative Experiment A. Experimental details are given in Table 1. The regression analysis for Experiment 1, using the $C_6$–$C_{28}$ contents, gives a nearly perfect Schulz-Flory distribution over the whole range of oligomers. The K-factor is 0.575 (for 12 observations $R^2$=0.99 and standard error=0.02). This is confirmed by the amount of waxy solids >$C_{28}$ isolated on total product of 0.3% wt, whereas the K-factor gives rise to a $C_{30}$–$C_{100}$ fraction on total oligomerisation product of 0.4% wt. Hence, no deviation from Schulz-Flory distribution is observed, which translates to the formation of less high molecular weight products in comparison with (comparative) Examples A–B.

In conclusion, it may be stated that using symmetrical 2,6-bis[1-(2,6-dihaloarylimine)alkyl]pyridine iron catalysts, ethylene oligomers can be produced according to a Schulz-Flory distribution while these catalysts have the advantage that they can be synthesised more readily than the previously described non-symmetrical catalysts developed for this purpose.

These experiments prove the beneficial effects which can be achieved with the catalyst systems of the present invention. As explained above, these improvements are of major importance for the economic attractiveness of the process.

TABLE 1

| Example No. | Ex. A (comp)[1,2] | Ex. B (comp)[2] | Ex. C (comp) | Ex. 1 |
|---|---|---|---|---|
| Iron Complex in Reactor (nmol) | 113 | 397 | 204 | 959 |
| Reaction Time (min) | 112 | 118 | 176 | 57 |
| Ethene Pressure MPa (bar(a)) | 1.6 (16) | 1.6 (16) | 1.6 (16) | 1.6 (16) |
| Ethene consumed (Total Product) (g) | 47.2 | 352.2 | 352.2 | 117.5 |
| Isolated Product < $C_{30}$ (g) | 14.1 | 288.2 | 322.8 | 92.1 |
| Isolated Solids > $C_{28}$ (g) | 25.4 | 39.0 | 23.4 | <0.1 |
| Solids > $C_{28}$ on Ethene (% wt) | 53.8 | 11.1 | 6.6 | <0.1 |
| $C_{30-100}$ on Total Product (calc'd) (% wt) | 12.2 | 7.0 | 8.2 | 0.1 |
| T.O.F (mol$C_2$ =/ molFe * h) | 7.98E + 06 | 1.62E + 07 | 2.10E + 07 | 4.58E + 06 |
| K-factor | 0.774 | 0.737 | 0.747 | 0.497 |
| 1 – $C_6$ = purity (% wt) | 99.5 | 99.1 | 99.7 | 97.9 |
| 1 – $C_{12}$ = purity (% wt) | 98.4 | 96.5 | 98.1 | 93.5 |

| Example No. | Ex. 2 | Ex. 3 | Ex. 4[1,3] |
|---|---|---|---|
| Iron Complex in Reactor (nmol) | 395 | 928 | 287 |
| Reaction Time (min) | 38 | 26 | 37 |
| Ethene Pressure MPa (bar(a)) | 1.6 (16) | 1.1 (11) | 1.6 (16) |
| Ethene consumed (Total Product) (g) | 117.3 | 117.9 | 58.9 |
| Isolated Product < $C_{30}$ (g) | 84.5 | 98.4 | 52.8 |
| Isolated Solids > $C_{28}$ (g) | <0.1 | <0.1 | n.d. |
| Solids > $C_{28}$ on Ethene (% wt) | <0.1 | <0.1 | n.d. |
| $C_{30-100}$ on Total Product (calc'd) (% wt) | 0.1 | 0.1 | n.d. |
| T.O.F (mol$C_2$ =/ molFe * h) | 1.67E + 07 | 1.03E + 07 | 1.19E + 07 |
| K-factor | 0.482 | 0.503 | 0.695[5] |
| 1 – $C_6$ = purity (% wt) | 96.9 | 94.9 | 98.0 |
| 1 – $C_{12}$ = purity (% wt) | 92.8 | 90.2 | 95.0 |

| Example No. | Ex. 5[4] | Ex. 6[6] |
|---|---|---|
| Iron Complex In Reactor (nmol) | 10800 | 8620 |
| Reaction Time (min) | 10 | 96 |
| Ethene Pressure MPa (bar(a)) | 1.6 (16) | 1.6 (16) |

TABLE 1-continued

| | | |
|---|---|---|
| Ethene consumed (Total Product) (g) | 22.1 | 111.5 |
| Isolated Product < $C_{30}$ (g) | 14.7 | 76.4 |
| Isolated Solids > $C_{28}$ (g) | 5.0 | 0.3 |
| Solids > $C_{28}$ on Ethene (% wt) | 22.6 | 0.3 |
| $C_{30-100}$ on Total Product (calc'd) (% wt) | 32.7 | 0.4 |
| T.O.F ($molC_2$ =/ molFe * h) | 4.38E + 05 | 2.88E + 05 |
| K-factor | 0.851 | 0.575 |
| 1 − $C_6$ = purity (% wt) | 97.0 | 87.2 |
| 1 − $C_{12}$ = purity (% wt) | 96.3 | 78.1 |

Experiments carried out at 50° C., at [Al]/[Fe] ratio of 1300–4600 in toluene, using 1-liter steel autoclave, unless indicated otherwise.
n.d. = Not Determined.
[1]Carried out in 0.5-liter steel autoclave.
[2]Catalyst prepared according to WO-A-99/02472.
[3]Carried out at 70° C.
[4]Complex 7 in toluene (without pre-activation) added to MAO/toluene mixture at [Al]/[Fe] ratio of 750.
[5]Combination of two Schulz-Flory K-factors.
[6]Due to relatively low activity several additions of Fe-complex required; final [AL]/[Fe] ratio = 500.

We claim:

1. A bis-aryliminepyridine ligand of formula (V), (V)

wherein $R_1$–$R_5$ and $R_7$–$R_9$ and $R_{12}$–$R_{14}$ are independently selected from the group consisting of hydrogen, optionally substituted hydrocarbyl, and inert groups, and $R_6$, $R_{10}$, $R_{11}$ and $R_{15}$ are identical and are selected from the group consisting of fluorine and chlorine.

2. The bis-aryliminepyridine ligand of claim 1, wherein $R_1$–$R_3$ are hydrogen; $R_4$ and $R_5$ are methyl; $R_7$–$R_9$ and $R_{12}$–$R_{14}$ are hydrogen; and $R_6$, $R_{10}$, $R_{11}$ and $R_{15}$ are fluorine.

3. The bis-aryliminepyridine ligand of claim 1, wherein $R_1$–$R_3$ are hydrogen; $R_4$ and $R_5$ are phenyl; $R_7$–$R_9$ and $R_{12}$–$R_{14}$ are hydrogen; and $R_6$, $R_{10}$, $R_{11}$ and $R_{15}$ are fluorine.

4. The bis-aryliminepyridine ligand of claim 1, wherein $R_1$–$R_3$ are hydrogen; $R_4$ and $R_5$ are hydrogen; $R_7$–$R_9$ and $R_{12}$–$R_{14}$ are hydrogen; and $R_6$, $R_{10}$, $R_{11}$ and $R_{15}$ are chlorine.

5. A bis-aryliminepyridine $MX_n$ complex comprising a ligand according to claim 1 wherein M is a metal atom selected from Fe and Co, n is 2 or 3, and X is halide, optionally substituted hydrocarbyl, alkoxide, amide, or hydride.

6. The bis-aryliminepyridine $MX_n$ complex of claim 5 wherein, in the ligand, $R_1$–$R_3$ are hydrogen; $R_4$ and $R_5$ are methyl; $R_7$–$R_9$ and $R_{12}$–$R_{14}$ are hydrogen; and $R_6$, $R_{10}$, $R_{11}$ and $R_{15}$ are fluorine.

7. The bis-aryliminepyridine $MX_n$ complex of claim 5 wherein, in the ligand, $R_1$–$R_3$ are hydrogen; $R_4$ and $R_5$ are phenyl; $R_7$–$R_9$ and $R_{12}$–$R_{14}$ are hydrogen; and $R_6$, $R_{10}$, $R_{11}$ and $R_{15}$ are fluorine.

8. The bis-aryliminepyridine $MX_n$ complex of claim 5 wherein, in the ligand, $R_1$–$R_3$ are hydrogen; $R_4$ and $R_5$ are hydrogen; $R_7$–$R_9$ and $R_{12}$–$R_{14}$ are hydrogen; and $R_6$, $R_{10}$, $R_{11}$ and $R_{15}$ are chlorine.

9. A {bis-aryliminepyridine $MY_p.L_n^+$} {$NC^-$}$_q$ complex comprising a ligand of claim 1, wherein: Y is a ligand adapted to insert an olefin; M is a metal atom selected from Fe and Co; $NC^-$ is a non-coordinating anion and p+q is 2 or 3, matching the formal oxidation of said metal atom; and L is a neutral Lewis donor molecule and n=0, 1, or 2.

10. The {bis-aryliminepyridine $MY_p.L_n^+$} {$NC^-$}$_q$ complex of claim 9 wherein, in the ligand, $R_1$–$R_3$ are hydrogen; $R_4$ and $R_5$ are methyl; $R_7$–$R_9$ and $R_{12}$–$R_{14}$ are hydrogen; and $R_6$, $R_{10}$, $R_{11}$ and $R_{15}$ are fluorine.

11. The {bis-aryliminepyridine $MY_p.L_n^+$} {$NC^-$}$_q$ complex of claim 9 wherein, in the ligand, $R_1$–$R_3$ are hydrogen; $R_4$ and $R_5$ are phenyl; $R_7$–$R_9$ and $R_{12}$–$R_{14}$ are hydrogen; and $R_6$, $R_{10}$, $R_{11}$ and $R_{15}$ are fluorine.

12. The {bis-aryliminepyridine $MY_p.L_n^+$} {$NC^-$}$_q$ complex of claim 9 wherein, in the ligand, $R_1$–$R_3$ are hydrogen; $R_4$ and $R_5$ are hydrogen; $R_7$–$R_9$ and $R_{12}$–$R_{14}$ are hydrogen; and $R_6$, $R_{10}$, $R_{11}$ and $R_{15}$ are chlorine.

13. A process for the production of alpha-olefins, which comprises contacting one or more complexes according to claim 5 with ethylene and an alkylaluminium compound which is adapted to transfer an optionally substituted hydrocarbyl or hydride group to said metal atom M, and which is also adapted to abstract an $X^-$ group from said metal atom, at a temperature in the range of −100° C. to 300° C.

14. A process for the production of alpha-olefins, which comprises contacting one or more complexes according to claim 6 with ethylene and an alkylaluminium compound adapted to transfer an optionally substituted hydrocarbyl or hydride group to said metal atom M, and which is also adapted to abstract an $X^-$ group from said metal atom, at a temperature in the range of −100° C. to 300° C.

15. A process for the production of alpha-olefins, which comprises contacting one or more complexes according to claim 7 with ethylene and an alkylaluminium compound which is adapted to transfer an optionally substituted hydrocarbyl or hydride group to said metal atom M, and which is also adapted to abstract an $X^-$ group from said metal atom, at a temperature in the range of −100° C. to 300° C.

16. A process for the production of alpha-olefins, which comprises contacting one or more complexes according to claim 8 with ethylene and an alkylaluminium compound which is adapted to transfer an optionally substituted hydrocarbyl or hydride group to said metal atom M, and which is also adapted to abstract an $X^-$ group from said metal atom, at a temperature in the range of −100° C. to 300° C.

17. A process for the production of alpha-olefins, which comprises contacting one or more complexes according to claim 5 with ethylene and an alkylaluminium compound which is adapted to transfer an optionally substituted hydrocarbyl or hydride group to said metal atom M, and a third compound which is also adapted to abstract an $X^-$ group from said metal atom, at a temperature in the range of −100° C. to 300° C.

18. A process for the production of alpha-olefins, which comprises contacting one or more complexes according to claim 6 with ethylene and an alkylaluminium compound which is adapted to transfer an optionally substituted hydrocarbyl or hydride group to said metal atom M, and a third compound which is also adapted to abstract an $X^-$ group from said metal atom, at a temperature in the range of $-100°$ C. to $300°$ C.

19. A process for the production of alpha-olefins, which comprises contacting one or more complexes according to claim 7 with ethylene and an alkylaluminium compound which is adapted to transfer an optionally substituted hydrocarbyl or hydride group to said metal atom M, and a third compound which is also adapted to abstract an $X^-$ group from said metal atom, at a temperature in the range of $-100°$ C. to $300°$ C.

20. A process for the production of alpha-olefins, which comprises contacting one or more complexes according to claim 8 with ethylene and an alkylaluminium compound which is adapted to transfer an optionally substituted hydrocarbyl or hydride group to said metal atom M, and a third compound which is also adapted to abstract an $X^-$ group from said metal atom, at a temperature in the range of $-100°$ C. to $300°$ C.

21. A process for the production of alpha-olefins, comprising contacting one or more {bis-aryliminepyridine $MY_p.L_n^+$} {$NC^-$}$_q$ complexes according to claim 9 with ethylene at a temperature in the range of $-100°$ C. to $300°$ C.

22. A process for the production of alpha-olefins, comprising contacting one or more {bis-aryliminepyridine $MY_p.L_n^+$} {$NC^-$}$_q$ complexes according to claim 10 with ethylene at a temperature in the range of $-100°$ C. to $300°$ C.

23. A process for the production of alpha-olefins, comprising contacting one or more {bis-aryliminepyridine $MY_p.L_n^+$} {$NC^-$}$_q$ complexes according to claim 11 with ethylene at a temperature in the range of $-100°$ C. to $300°$ C.

24. A process for the production of alpha-olefins, comprising contacting one or more {bis-aryliminepyridine $MY_p.L_n^+$} {$NC^-$}$_q$ complexes according to claim 12 with ethylene at a temperature in the range of $-100°$ C. to $300°$ C.

25. The process of claim 13 wherein ethylene is contacted with one or more additional complexes adapted to produce of alpha olefins.

26. The process of claim 14 wherein ethylene is contacted with one or more additional complexes adapted to produce alpha olefins.

27. The process of claim 15 wherein ethylene is contacted with one or more additional complexes adapted to produce alpha olefins.

28. The process of claim 16 wherein ethylene is contacted with one or more additional complexes adapted to produce alpha olefins.

29. The process of claim 17 wherein ethylene is contacted with one or more additional complexes adapted to produce alpha olefins.

30. The process of claim 18 wherein ethylene is contacted with one or more additional complexes adapted to produce alpha olefins.

31. The process of claim 19 wherein ethylene is contacted with one or more additional complexes adapted to produce alpha olefins.

32. The process of claim 20 wherein ethylene is contacted with one or more additional complexes adapted to produce alpha olefins.

33. The process of claim 21 wherein ethylene is contacted with one or more additional complexes adapted to produce alpha olefins.

34. The process of claim 22 wherein ethylene is contacted with one or more additional complexes adapted to produce alpha olefins.

35. The process of claim 23 wherein ethylene is contacted with one or more additional complexes adapted to produce alpha olefins.

36. The process of claim 24 wherein ethylene is contacted with one or more additional complexes adapted to produce alpha olefins.

37. A bis-aryliminepyridine ligand of formula (V), (V)

wherein $R_1$–$R_5$ and $R_7$–$R_9$ and $R_{12}$–$R_{14}$ are each, independently, hydrogen, optionally substituted hydrocarbyl, or halogen, and $R_6$, $R_{10}$, $R_{11}$ and $R_{15}$ are identical and are selected from fluorine or chlorine.

38. A bis-aryliminepyridine ligand according to claim 37 wherein $R_1R_3$ are hydrogen; $R_4$ and $R_5$ are methyl; $R_7$–$R_9$ and $R_{12}$–$R_{14}$ are hydrogen; and $R_6$, $R_{10}$, $R_{11}$ and $R_{15}$ are fluorine.

39. A bis-aryliminepyridine ligand according to claim 37 wherein $R_1$–$R_3$ are hydrogen; $R_4$ and $R_5$ are hydrogen; $R_7$–$R_9$ and $R_{12}$–$R_{14}$ are hydrogen; and $R_6$, $R_{10}$, $R_{11}$ and $R_{15}$ are chlorine.

40. A bis-aryliminepyridine $MX_n$ complex consisting essentially of a ligand according to claim 37 wherein M is a metal atom selected from Fe and Co, n is 2 or 3, and X is halide, optionally substituted hydrocarbyl, alkoxide, amide, or hydride.

41. A bis-aryliminepyridine $MX_n$ complex consisting essentially of a ligand according to claim 38 wherein M is a metal atom selected from Fe and Co, n is 2 or 3, and X is halide, optionally substituted hydrocarbyl, alkoxide, amide, or hydride.

42. A bis-aryliminepyridine $MX_n$ complex consisting essentially of a ligand according to claim 39 wherein M is a metal atom selected from Fe and Co, n is 2 or 3, and X is halide, optionally substituted hydrocarbyl, alkoxide, amide, or hydride.

43. A {bis-aryliminepyridine $MY_p.L_n^+$} {$NC^-$}$_q$ complex consisting essentially of a ligand according to claim 37 wherein Y is a ligand adapted to insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

44. A {bis-aryliminepyridine $MY_p.L_n^+$} {$NC^-$}$_q$ complex consisting essentially of a ligand according to claim 38 wherein Y is a ligand adapted to insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

45. A {bis-aryliminepyridine $MY_p.L_n^+$} {$NC^-$}$_q$ complex consisting essentially of a ligand according to claim 39 wherein Y is a ligand adapted to insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

46. A {bis-aryliminepyridine $MY_p.L_n^+$} {$NC^-$}$_q$ complex consisting essentially of a ligand according to claim 40 wherein Y is a ligand adapted to insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

47. A {bis-aryliminepyridine $MY_p.L_n^+$} {$NC^-$}$_q$ complex consisting essentially of a ligand according to claim 41 wherein Y is a ligand adapted to insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

48. A {bis-aryliminepyridine $MY_p.L_n^+$} {$NC^-$}$_q$ complex consisting essentially of a ligand according to claim 42 wherein Y is a ligand adapted to insert an olefin; M is a metal atom selected from Fe and Co, $NC^-$ is a non-coordinating anion and p+q is 2 or 3, matching the formal oxidation of said metal atom; L is a neutral Lewis donor molecule and n=0, 1, or 2.

\* \* \* \* \*